United States Patent [19]

Duffett et al.

[11] Patent Number: Plant 6,499

[45] Date of Patent: Dec. 27, 1988

[54] CHRYSANTHEMUM PLANT NAMED DART

[75] Inventors: William E. Duffett; Cornelis P. VandenBerg, both of Salinas, Calif.

[73] Assignee: Yoder Brothers, Inc., Barberton, Ohio

[21] Appl. No.: 49,832

[22] Filed: May 15, 1987

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Evans

[57] ABSTRACT

A Chrysanthemum plant named Dart particularly characterized by its flat capitulum form; spooned daisy capitulum type; red-purple ray floret color; diameter across face of capitulum of up to 12 cm at maturity; uniform nine week photoperiodic flowering response to short days; medium plant height when grown single stem; 15 to 25 cm peduncles on open, normally terminal sprays; and 13 degrees Celsius minimum temperature tolerance for initiation and development of flowering buds with a 12 to 13 hour continuous dark period.

3 Drawing Sheets

The present invention comprises a new and distinct cultivar of Chrysanthemum, botanically known as *Chrysanthemum morifolium,* Ramat., and referred to by the cultivar name Dart.

Dart, identified as 80633002, was originated from a cross made in a controlled breeding program in Salinas, Calif., in 1980.

The female parent of Dart, identified as 78546013, was an unnamed seedling. The male parent of Dart, identified as 77064005, was also an unnamed seedling.

Dart was discovered and selected as one flowering plant within the progeny of the stated cross by William E. Duffett in September, 1981, in a controlled environment in Salinas, Calif.

The first act of asexual reproduction of Dart was accomplished when vegetative cuttings were taken from the initial selection in November, 1981, in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Dart are firmly fixed and are retained through successive generations of asexual reproduction.

Dart has not been observed under all possible environmental conditions. The phenotype may vary significantly with variations in environment such as temperature, light intensity and daylength.

The following observations, measurements and comparisons describe plants grown in Salinas, Calif., and Leamington, Canada, under greenhouse conditions which approximate those generally used in commercial greenhouse practice.

The following traits have been repeatedly observed and are determined to be basic characteristics of Dart, which, in combination, distinguish this Chrysanthemum as a new and distinct cultivar:

1. Flat capitulum form.
2. Spooned daisy capitulum type.
3. Red-purple ray floret color.
4. Diameter across face of capitulum up to 12 cm at maturity.
5. Uniform nine week photoperiodic flowering response to short days.

6. Peduncle length ranging from 15 to 25 cm.
7. Medium plant height, requiring two long day weeks prior to short days to attain a flowered plant height of 100 to 110 cm for year-round flowerings.
8. Low temperature tolerance of 13 degrees Celsius for initiation and development when grown in single stem cut spray programs with a continuous dark period of 12 to 13 hours.

The accompanying photographic drawings show typical inflorescence and leaf characteristics of Dart, with the colors being as nearly true as possible with illustrations of this type. Sheet 1 is a color photograph of Dart grown as a single stem cut spray. Sheet 2 is a black and white photograph of three views of the inflorescence of Dart. Sheet 3 is a black and white photograph showing the upper and under sides of the leaves of Dart at three stages of development (mature, intermediate and immature).

The combination of capitulum type and floret color is not represented in comparable commercial cultivars known to the inventors. Capitulum form and type are similar to Futura, a yellow spooned daisy, disclosed in U.S. Plant Pat. No. 4,622. The diameter across face of capitulum of Dart is slightly larger than that of Futura, being 12 and 11 cm, respectively. Plant height and flowering response to short days of Dart is similar to those same characteristics of Blue Marble, unpatented.

In the following description color references are made to The Royal Horticultural Society Colour Chart. The color values were determined on plant material grown in Salinas, Calif., on Oct. 17, 1986.

Classification:

*Botanical.*—*Chrysanthemum morifolium,* Ramat., cv. Dart.

*Commercial.*—Spooned daisy cut spray mum.

INFLORESCENCE

A. Capitulum:

*Form.*—Flat.

*Type.*—Spooned daisy.

*Diameter across face.*—Up to 12 cm at maturity.

B. Corolla of ray florets:

*Color (general tonality from a distance of three meters).*—Red-purple.

*Color (upper surface, spoon tips).*—70A.

*Color (under surface and tubes).*—76C, slightly streaked with 78D.

*Shape.*—Base tubular. Distal portion open, flattened and spoon like.

C. Corolla of disc florets:

*Color (mature).*—12B.

*Color (immature).*—144B.

D. Reproductive organs:

*Androecium.*—Present on disc florets only; moderate pollen.

*Gynoecium.*—Present on both ray and disc florets.

PLANT

A. General appearance:

*Height.*—Medium; 100 to 110 cm as a flowering plant when grown single stem from a rooted cutting with two long day weeks for year-round flowerings maintaining a continuous dark period of 12 to 13 hours.

B. Foliage:

*Color (upper surface).*—147A.

*Color (under surface).*—147B.

*Shape.*—Deeply lobed, slightly serrated.

We claim:

1. A new and distinct plant of Chrysanthemum named Dart, as described and illustrated, and particularly characterized as to uniqueness by the combined characteristics of flat capitulum form; spooned daisy capitulum type; red-purple ray floret color; diameter across face of capitulum of up to 12 cm at maturity; uniform nine week photoperiodic flowering response to short days; medium plant height when grown single stem; 15 to 25 cm peduncles on open, normally terminal sprays; and 13 degrees Celsius minimum temperature tolerance for initiation and development of flowering buds.

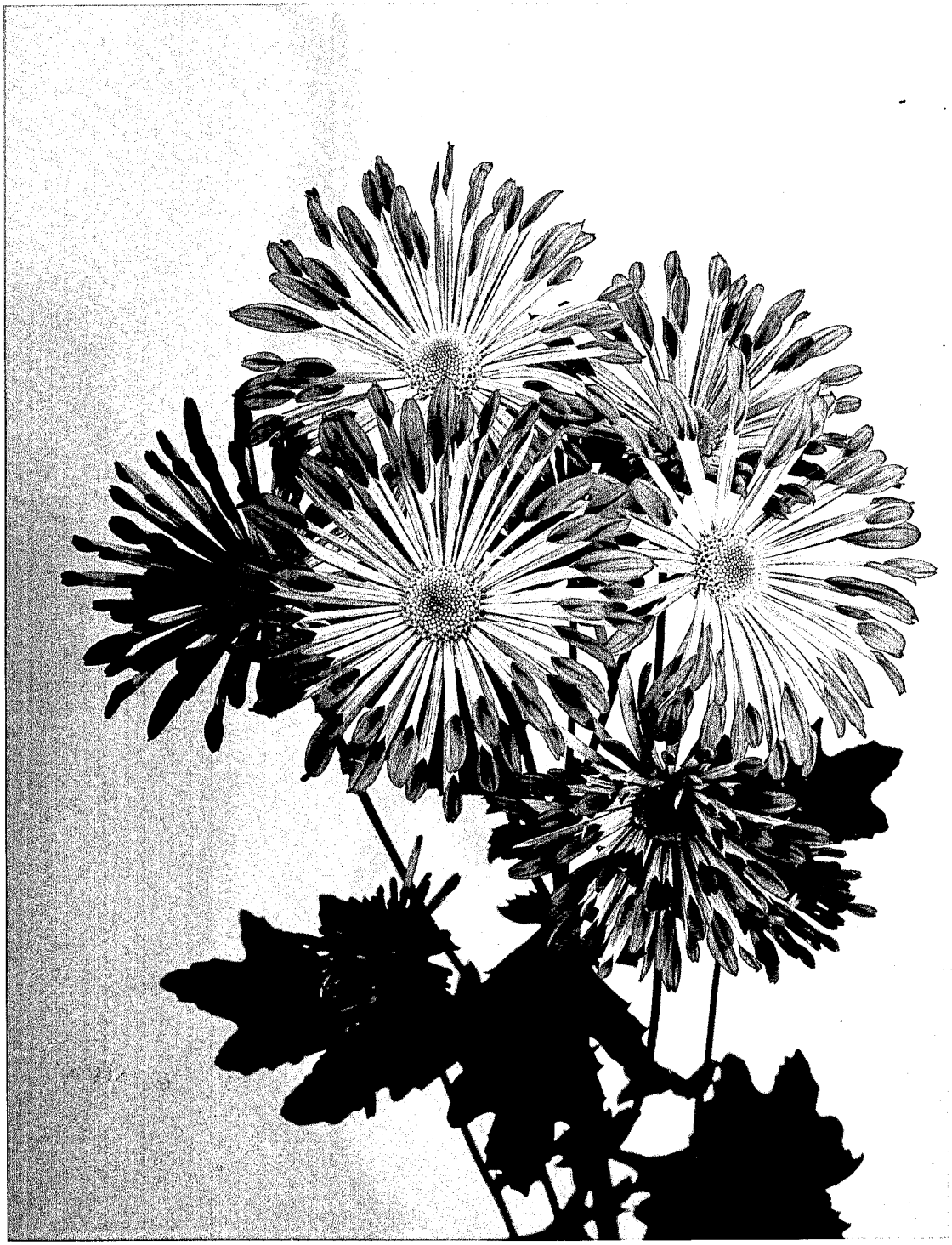

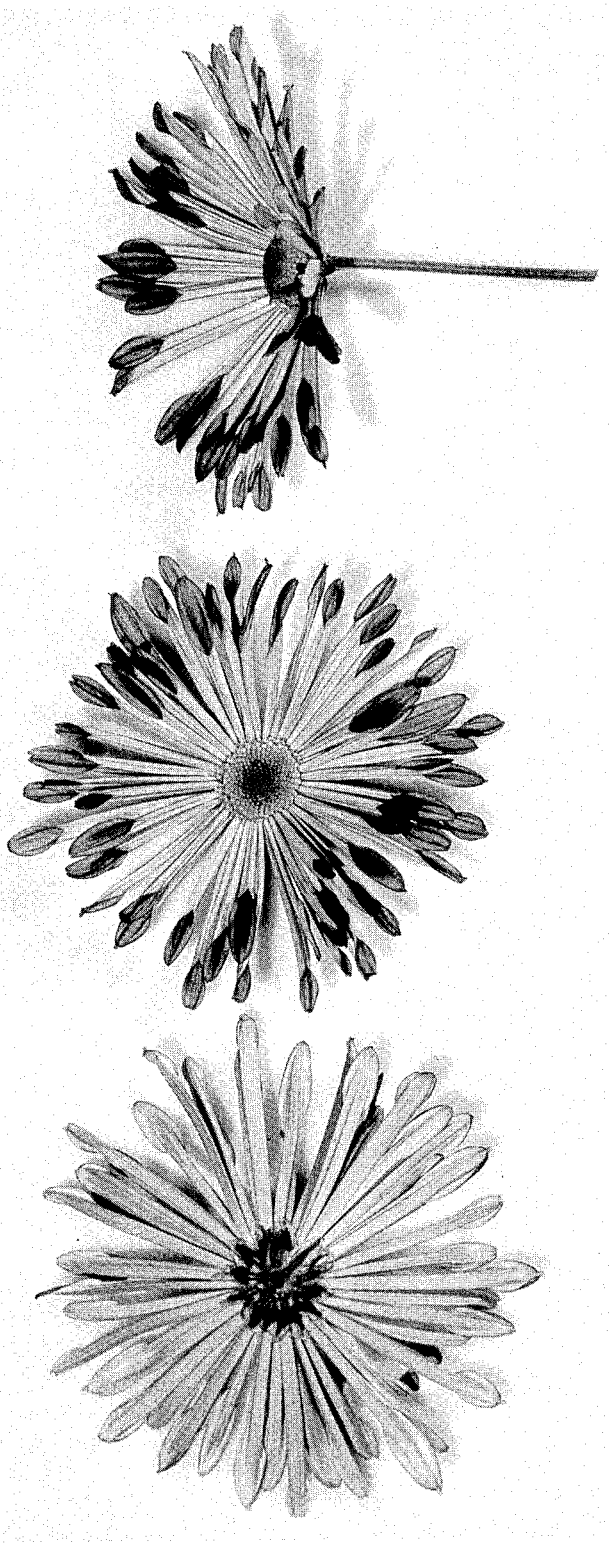

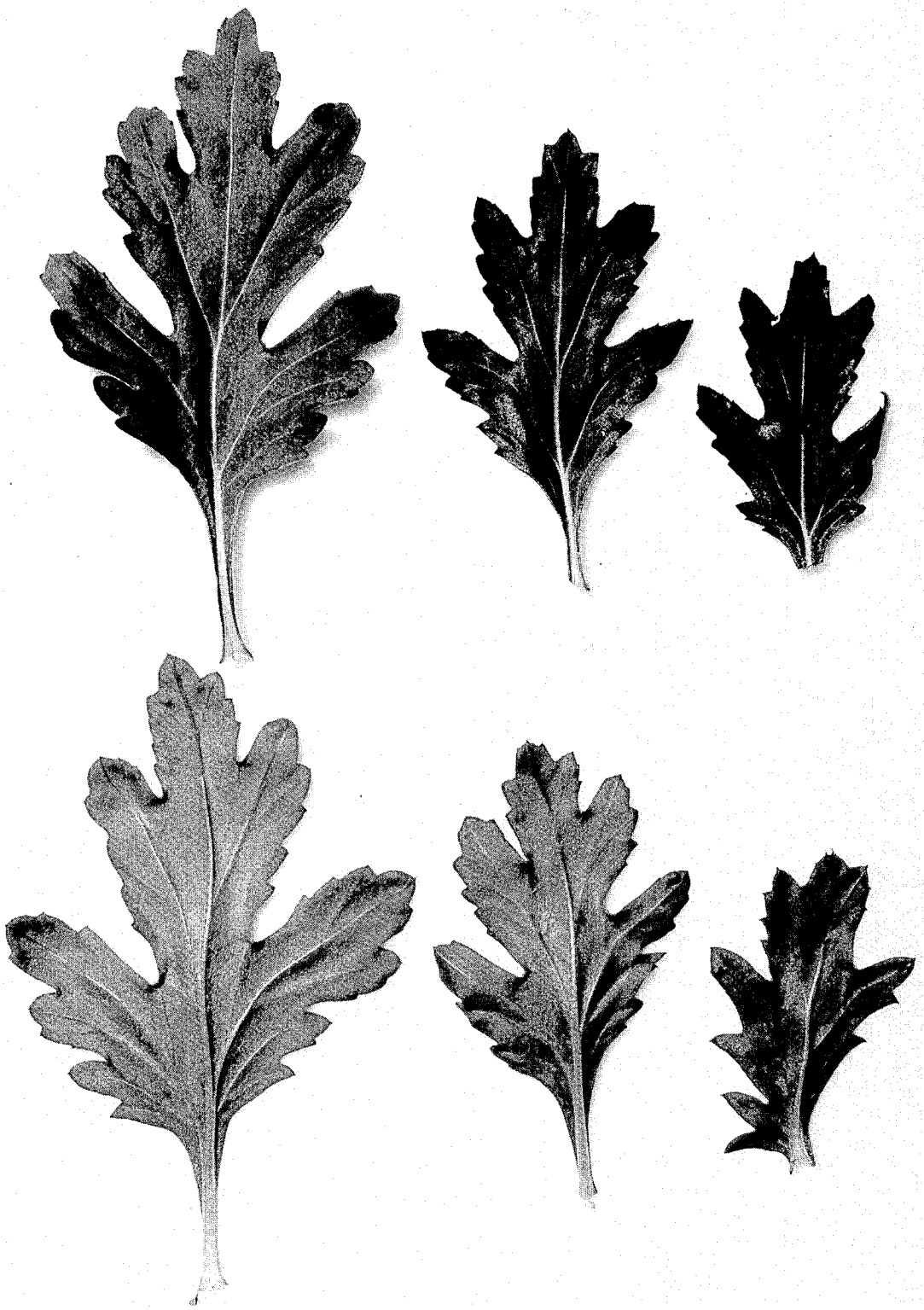

* * * * *